United States Patent [19]

Boudy

[11] Patent Number: 4,583,408
[45] Date of Patent: Apr. 22, 1986

[54] APPARATUS TO EVALUATE BUBBLE FORMATION

[75] Inventor: Francois Boudy, Champs-sur-Marne, France

[73] Assignee: General Foods France, Reuil Malmaison, France

[21] Appl. No.: 597,962

[22] Filed: Apr. 9, 1984

[30] Foreign Application Priority Data

Apr. 12, 1983 [FR] France ............................... 83 05948

[51] Int. Cl.⁴ ............................................. G01N 3/10
[52] U.S. Cl. .................................................... 73/840
[58] Field of Search ...................... 73/840, 64.4, 169

[56] References Cited

U.S. PATENT DOCUMENTS 2,826,063  3/1958  Astley ..................................... 73/840

Primary Examiner—Stephen A. Kreitman
Attorney, Agent, or Firm—Linn I. Grim; Thomas R. Savoie; Daniel J. Donovan

[57] ABSTRACT

An apparatus is provided to determine the film forming properties of a paste, especially a paste of chewing gum or bubble gum, in order to evaluate its bubble-forming ability and a process for using this apparatus.

12 Claims, 8 Drawing Figures

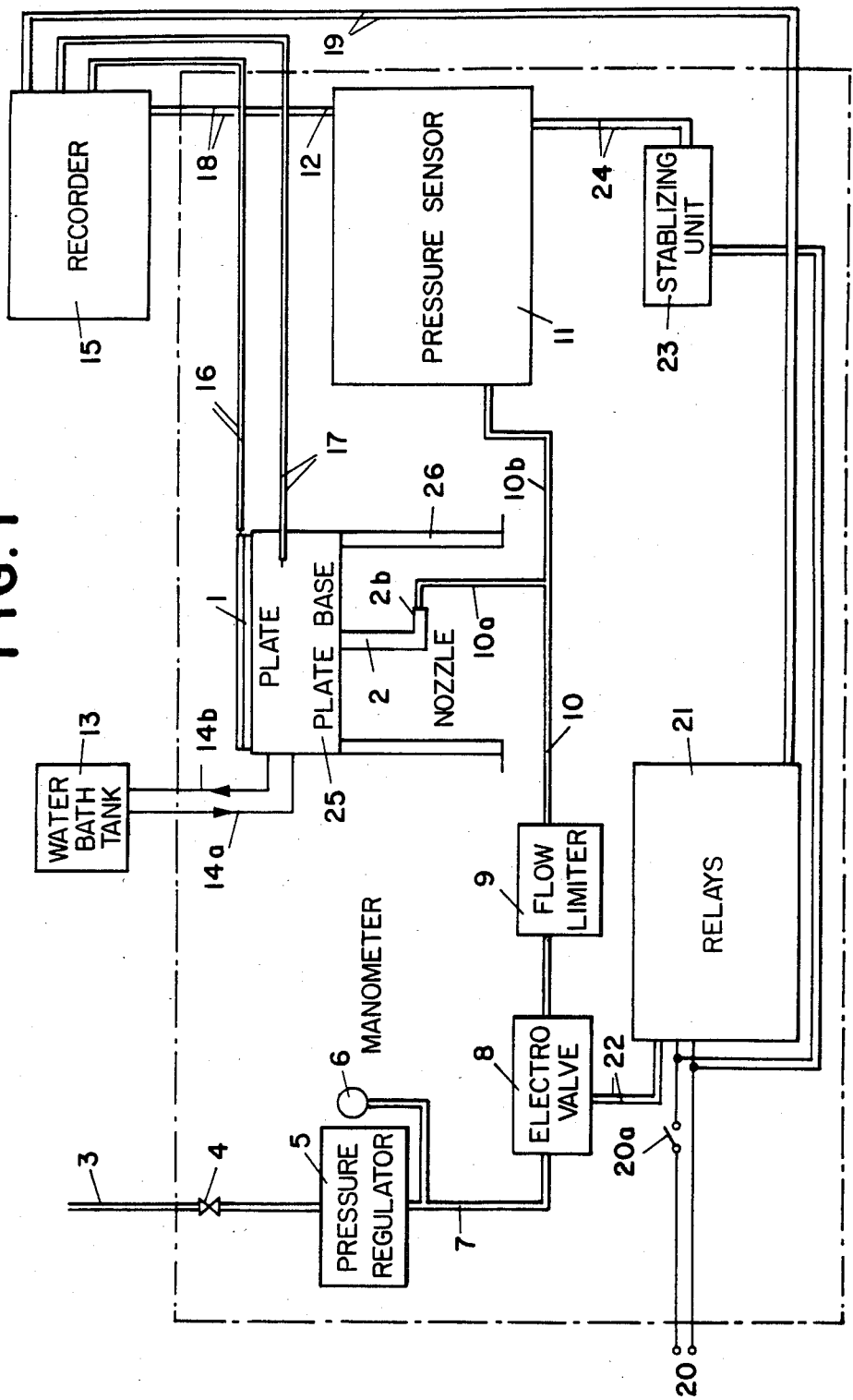

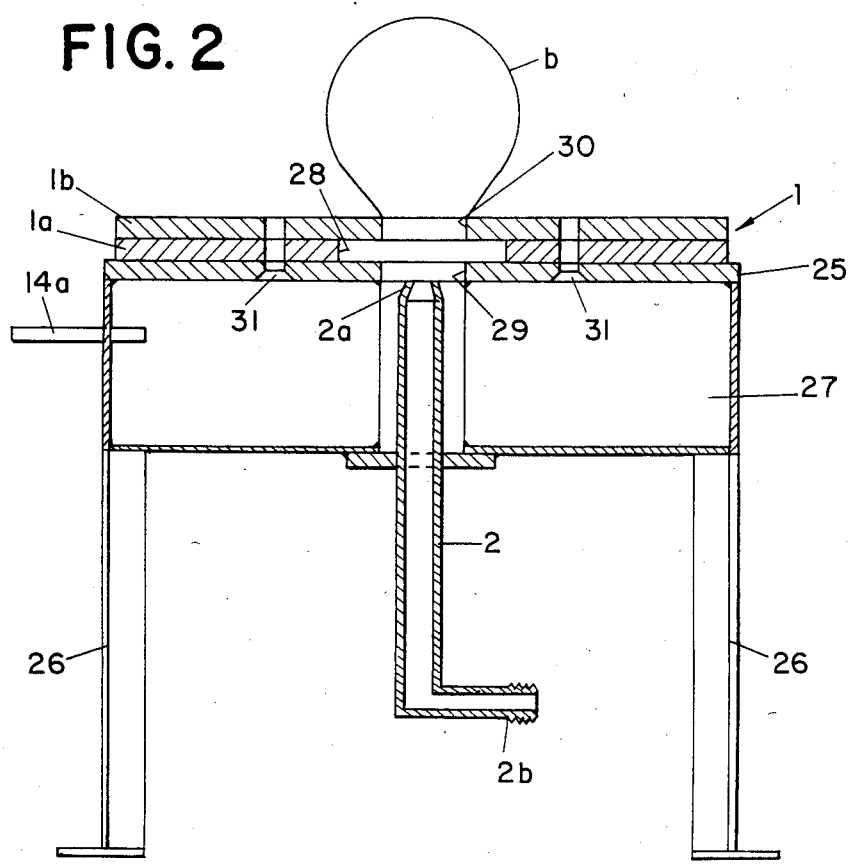
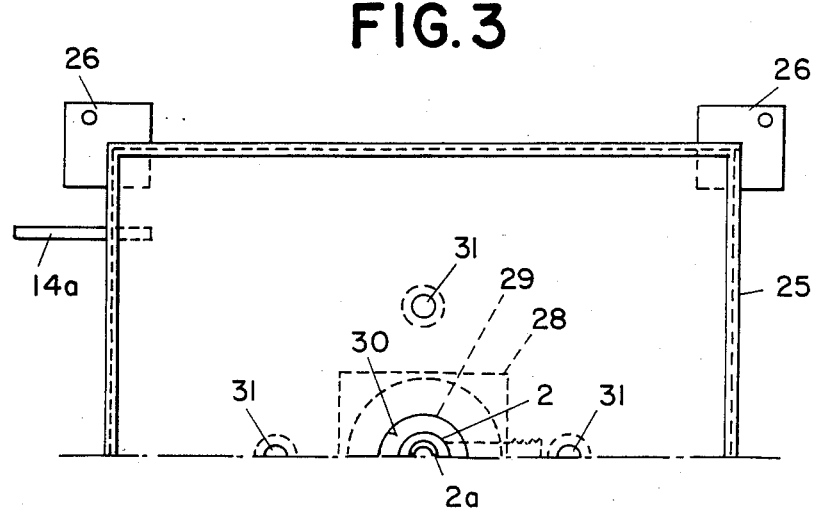

APPARATUS TO EVALUATE BUBBLE FORMATION

BACKGROUND OF THE INVENTION

1. Field of the Invention

The present invention concerns the determination of the film-forming properties of a paste.

It may relate to a paste or dough obtained from cereal flour and in this case the apparatus according to the invention permits the ability of the flour to make bread or biscuits to be evaluated.

It particularly concerns, in the preferred application of the invention, a paste of chewing gum and more precisely bubble gum, and in this case the apparatus according to the invention permits the ability of this paste to form bubbles to be evaluated.

Hereinafter, and especially in the description, the application to a bubble gum paste will be discussed exclusively.

In relation to this subject it will be recalled that the essential characteristic of a bubble gum is its ability to form bubbles whilst being chewed by the person who has put it into his mouth.

This ability derives from the composition of the base gum, which forms the insoluble part of the bubble gum (the masticatory support) and to the properties of the starting materials used.

As a result, when a bubble gum manufacturer wishes to develop and put on the market a new base gum, he must determine the ability of the paste of this bubble gum to form bubbles under the effect of mastication.

2. Description of the Prior Art

From time to time, qualitative determinations of the ability of a bubble gum paste to form bubbles have been made by resorting to a group of experts who chew this paste, but the problems posed by such experiments, which are of necessity subjective and do not give true numerical results, will be readily understood.

It has also been proposed to make use of a traction machine which acts on a dumb-bell shaped test sample of bubble gum base gum. This is however a linear test, in other words according to only one axis, along which the traction is exerted, whilst the inflation of a bubble is a surface effect, which thus is dependent on two axes. The numerical results of a traction test do not therefore permit sufficiently precise determination of the ability of a gum for bubble gum to form bubbles.

In order to determine the said ability, apparatus intended for the evaluation of the ability of a flour or cereal dough to make bread or biscuits, for example a Chopin alveograph (from the company Chopin S.A.), has occasionally been used. In an alveograph of this sort a sample of paste is submitted to a pressure supplied by means of a column of water disposed above the alveograph proper, this pressure bringing about the inflation of a bubble of paste. The pressure variation caused by the formation of the bubble is determined during the inflation period by means of a column of mercury. The measurements obtained with apparatus of this type do not permit the properties of base gums for bubble gum to be ascertained in a satisfactory manner, owing to the performance of the apparatus.

SUMMARY OF THE PRESENT INVENTION

The object of the present invention is therefore to provide an apparatus which permits the film-forming properties of a paste to be measured with great precision, and especially bubble gum paste, so as to determine its ability to form bubbles when it is masticated, and a process for using such apparatus.

An apparatus according to the invention includes in combination:

plate means comprising a lower plate with a recess for the sample under test and an upper counter-plate arranged on the lower plate, the counter-plate also having a through opening which is located opposite to the said recess;

means to bring the plate to and maintain it at the temperature desired for the test;

a nozzle arranged beneath the lower plate, and at a certain distance from it, the axis of the nozzle corresponding to the centres of the openings in the plate and counter-plate;

means to supply air under pressure to the said nozzle;

means to control the pressure, and possibly the flow, of the air supply to the said nozzle; and means to determine the variation in the pressure, as a function of time, at the bubble formed in the sample.

The process in which this apparatus is used in the testing of bubble gum consists in:

hydrating, to a predetermined degree, the base gum to be tested to confer on it substantially the same consistency that is has in the mouth during mastication, forming samples from the hydrated gum of a size appropriate for lodgement in the plate means of the apparatus which is to receive the samples, pre-heating the samples, introducing a first pre-heated sample into the said recess, awaiting temperature setting of the plate means and the sample by the said means for bringing the plate means to and maintaining it at the temperature desired for the test, supplying the nozzle with air under pressure, and determining the variation in pressure at the bubble which is formed in the sample, especially by commencement, either manually or automatically, of recording of the pressure-temperature curve, by the said means to determine the variation in pressure as a function of time, repeating the successive operations of sample introduction, temperature setting of the plate means and the sample, and commencement of recording, for successive samples in the case where several tests are being made on the same base gum.

Other objects and features of the invention will become apparent from the following description and the attached drawings, which are of course given by way of example only.

BRIEF DESCRIPTION OF THE DRAWINGS

FIG. 1 shows schematically one complete form of apparatus according to the invention.

FIG. 2 is a vertical sectional view of the plate means of the apparatus of FIG. 1, with the nozzle (also in section) and the supporting feet of the plate means, a bubble being shown during the course of formation.

FIG. 3 is a partial plan view, from above, of the plate means, the nozzle and its supporting feet.

Finally.

DETAILED DESCRIPTION OF THE PREFERRED EMBODIMENTS

Figure 4:
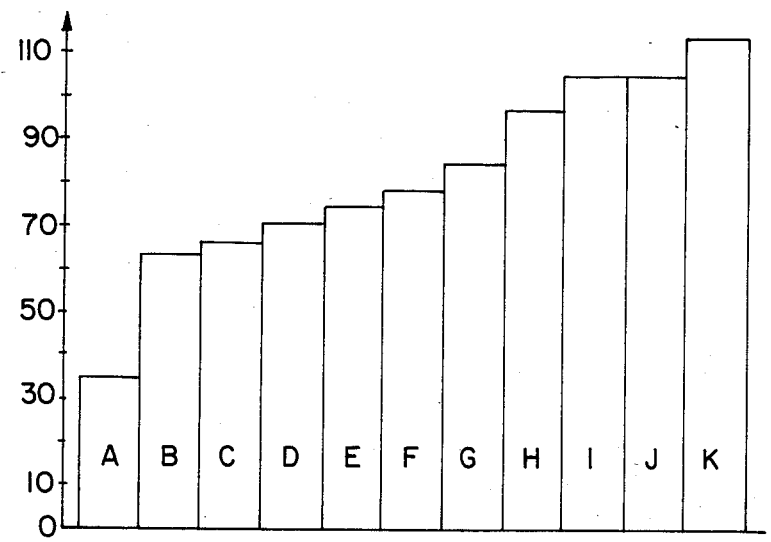
FIGS. 4 to 6 give the results of tests on various base gums, showing respectively the height in millimeters of the pressure peak during recording, the surface area in $mm^2 \times 10$ of the pressure peak during recording and the length of the test.

The apparatus taken as a whole (FIG. 1) comprises firstly thermostatic plate means 1, to receive the successive samples or wads, with the nozzle 2, the assembly of the plate means, and the nozzle being described in more detail hereinafter with reference to FIGS. 2 and 3.

The apparatus further includes a pneumatic system formed by:

an inlet line 3 for air under pressure (for example clean dry air under a pressure of between 2 and 4 bars), for example from an air compressor or from a compressed air distribution system;

a stop valve 4;

a pressure regulator 5;

a manometer 6 which permits the pressure at the entrance to the conduit 7 to be measured;

the conduit 7 which supplies the compressed air at the pressure determined by the manometer 6;

an electrovalve 8, a flow limiter 9;

a conduit 10 which supplies, via its branch 10a the nozzle 2, and also, via its branch 10b, a pressure sensor 11; and a pressure sensor 11 which emits at 12 a signal proportional to the pressure in the conduit 10 and its branches 10a and 10b, and thus at the base 2b of the nozzle 2.

The apparatus also includes:

a water-bath tank 13 (or for another heat-carrying fluid) which, by circulation within the passages 14a, 14b in the direction of the arrows, ensures temperature control of the plate means 1;

a single track or preferably multi-track recorder 15, which receives signals representing the temperature of the sample via the conductors 16, the temperature of the plate means via the conductors 17, and the pressure within the nozzle 2, as detected by the sensor 11, via the conductors 18, and also, via the conductors 19, a command to advance or to arrest the paper or other support on which the record curves are traced.

Finally the apparatus of the invention includes an electrical portion which comprises:

a power supply lead 20 (for example at 220 volts, 50 Hz) with a circuit-breaker 20a;

an assembly of relays 21 which control the electrovalve 8 via conductors 22 and the starting or stopping of recording via the conductors (19); and a stabilizing unit 23 for the voltage which supplys the pressure sensor 11 at a stabilized voltage (for example at 127 volts±1%) via the conductors 24.

There will now be described, with reference to FIGS. 2 and 3, the plate means 1 and the associated nozzle.

The plate means 1 comprises a base 25 supported by four feet 26. The base 25 may be brought to and maintained at the desired temperature (for example 38° C.) by the circulation of a heat-carrying fluid, such as water, as has previously been explained, the fluid arriving from the tank 13 via the conduit 14a, circulating through a chamber 27, and leaving by the conduit 14b (not shown in FIGS. 2 and 3) to return to the tank 13.

The nozzle 2 is arranged at the centre of the plate 25 and the feet 26 and terminates in an inflation jet 2a, whilst its other end 2b is threaded to receive, by means of a joint, compressed air from branch 10a of the conduit 10.

The plate means proper is formed by a plate 1a and a counter-plate 1b.

The plate 1a, carried by the base 25, is perforated at its centre by a recess 28 (to receive a sample of paste to be tested), which is preferably square and larger in size than the opening 29, which is preferably round, and located at the centre of the base 25.

It will be noted that the upper part 2a of the nozzle 2 is arranged at a certain distance beneath the recess 28.

The counter-plate 1b is perforated with a central orifice which is preferably circular.

Screws 31 allow assembly of the plate 1a onto the base 25. The counter-plate 1b may be fixed to the plate 1a either by the same screws 31, or by other means.

Thermo-couples (not shown), located in the recess 28 of the plate 1a, have their outlets connected respectively to the conductors 16 and 17.

The method of using the apparatus which has just been described with reference to FIGS. 1 to 3 is as follows:

A paste, hydrated for example to 10%, is first prepared from the base gum which it is desired to test, in that the ability of the base gum to form bubbles can be measured conveniently only in the hydrated state. The hydrated product is kneaded manually to form a rectangular cake which is flattened to a final thickness of for example 5 mm. Square samples or wads having the same dimensions as the recess 28 in the plate 1a, for example 40×40 mm, are then cut out from it using a scalpel.

Before measurements are taken and so as to standardise the test, the samples are brought to a particular temperature, which is always the same, for example by placing them for an hour in an oven maintained at 40° C. The samples are not removed from the oven until immediately before they are to be tested.

The apparatus shown in FIGS. 1 and 3 is then prepared by first opening the valve 4 which allows the compressed air to enter. A thermostat for the circulation of the heat-carrying fluid is then adjusted, the temperature being available from the conductors 17 (the temperature-controlled thermostat for the circulation of fluid is not shown in FIG. 1). The temperature of the fluid is for example controlled so that a temperature of 38° C. is attained within the chamber 27, the plate means then having a temperature of 37° C. (available from the conductors 16). The pressure of admission of compressed air into the nozzle 2 is then adjusted by operating the pressure regulator 5 and flow limiter 9. The air supply is then cut off.

The sample can then be removed from the oven and positioned in the recess 28. The plate means is closed and, when its temperature has reached the desired value (37° C.), inflation is commenced by operating the electrovalve 8, and also commencement of recording using the recorder 15. In a preferred, automatic, embodiment, these two operations are initiated simultaneously by the assembly of relays 21.

The bubble b (FIG. 2) then forms as a result of deformation of the sample located within the recess 28, the lower part of the bubble b fitting against the periphery of the orifice 30 (which is preferably circular in section). The manner of formation of the bubble b is observed and as soon as the volume of the bubble ceases to increase or as soon as the bubble begins to leak, the assembly of relays 21 is actuated to interrupt both the inlet of air through the conduit 10 and recording by means of the recording device 15. In general four or five tests are carried out on each base gum.

Figure 8:
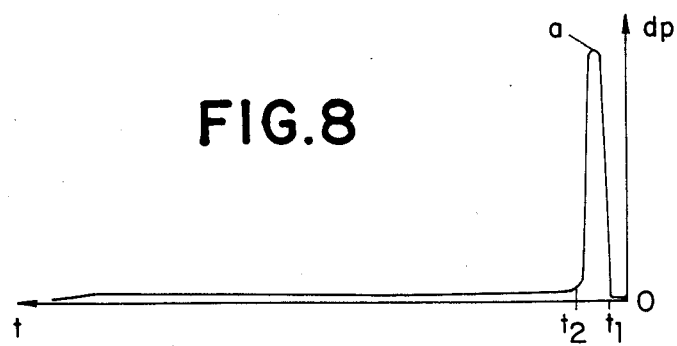
FIG. 8 illustrates a typical recorded curve.

A record of the variation in pressure dp as a function of the time t is shown in FIG. 8, formation of the bubble commencing at the instant $t_1$ and the development of the bubble ceasing at the instant $t_2$. A peak a is obtained.

The following values are determined from the curve shown in FIG. 8;

the height of the peak (in mm on the graph), the surface area of the peak (in $mm^2$ on the graph) and the length of the test (in mm recorded).

Figure 5:
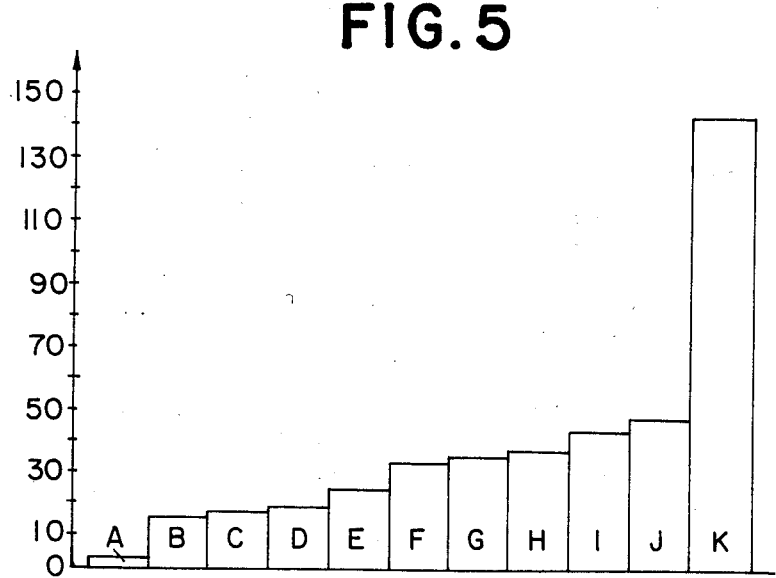
Figure 6:
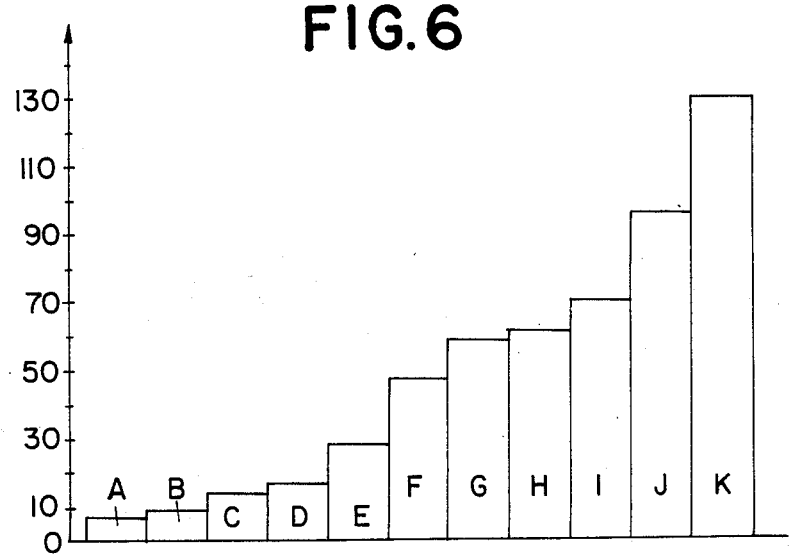

The results of the tests on 11 base gums designated by the letters A, B, C, D, E, F, G, H, I, J, K are shown in FIGS. 4, 5 and 6 by rectangles. The heights of the rectangles corresponding to the respective base gums represent the heights of the peaks in millimeters in FIG. 4, the surface area of the peaks in $mm^2 \times 10$ in FIG. 5, and the lengths of the tests (in mm of the graph) in FIG. 6.

It will be seen that the values of these three parameters do not rank in the same order for the different base gums tested.

The height of the peaks and the surface area of the peaks are related to the resistance of the hydrated base gum, i.e. to inflation of the bubble, the height of the peak (FIG. 4) being essentially representative of the initial resistance to inflation, whilst the surface under the peak (FIG. 5) is essentially representative of the overall resistance of the hydrated gum to the formation of the bubble.

Finally, the length of the test (FIG. 6) is related to the volume of the bubble formed.

By way of comparison, two curves are shown in FIG. 7, again for the gums A to K, the length of the test corresponding to the volume of the bubbles (the curve in broken lines) and the surface area under the peaks showing the overall resistance to inflation of the gum (the curve in full lines).

Figure 7:
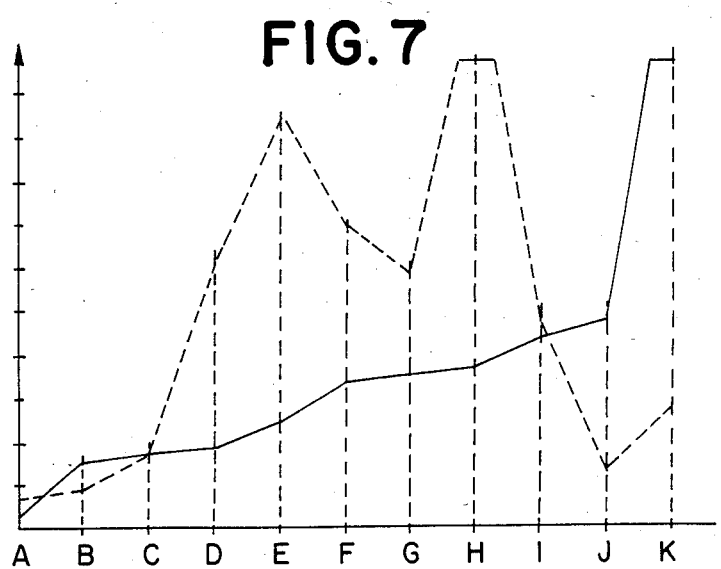
FIG. 7 is a graph illustrating by means of curves, for base gums which have been tested, the values of the length of the test (the curve in broken lines) and the surface under the peaks (the curve in full lines).

FIG. 7 shows that the two parameters do not vary in the same way, but permits selection from knowledge of the preferred base gum from amongst the gums tested.

As goes without saying and as is also apparent from the foregoing, the invention is in no way limited to those embodiments of application and construction which have been described in detail. On the contrary, it includes all variations.

I claim:

1. Apparatus to determine the film-forming properties of a paste sample, especially a paste of chewing gum or bubble gum in order to evaluate its ability to form bubbles, said apparatus comprising:

plate means including a lower plate having a recess for a sample under test and an upper counter-plate located on the lower plate, said counter-plate also being perforated with an opening located opposite the said recess;

means to bring the plate means to and maintain it at the temperature desired for the test;

a nozzle arranged at a certain distance beneath said lower plate the axis of said nozzle corresponding to the centres of the openings in said plate and counter-plate;

means to supply air under pressure to said nozzle;

means to control the pressure, and possibly the flow rate, of the air supply to said nozzle; and means to determine the variation in the pressure, as a function of time, at the bubble formed in said sample.

2. Apparatus according to claim 1, which also includes means to measure the general inlet pressure.

3. Apparatus according to claim 1, wherein said sample recess located in said lower plate is of square section.

4. Apparatus according to claim 1, wherein said opening located in said counter-plate is circular.

5. Apparatus according to claim 1, wherein the inflation end of said nozzle is disposed at a particular distance below said lower plate of said plate means.

6. Apparatus according to claim 1, including means to record the variation in pressure at said bubble as a function of time.

7. Apparatus according to claim 6 including means to control simultaneously the supply of compressed air to said nozzle and the commencement of operation of said recording means.

8. Apparatus according to claim 1 wherein said means to determine the variation in pressure at the bubble includes pressure detector means located externally of said plate means.

9. Apparatus according to claim 1, including means to measure continuously the temperature of said sample.

10. A method of using an apparatus to determine the film forming properties which comprises:

hydrating to a predetermined degree a base gum to be tested to confer on it substantially the consistency which it possesses in the mouth during mastication, forming at least one sample from said hydrated gum having dimensions appropriate to said recess in the plate means of the apparatus which is to receive the samples, pre-heating said sample, introducing said sample into the said recess, awaiting setting of the temperature of the plate means and the sample by virtue of said means to bring the plate means to and maintain it at the temperature desired for the test, supplying compressed air to said nozzle, and determining the pressure variations at the bubble which forms within said sample, using the said means to determine the pressure variations as a function of time.

11. Method according to claim 10, wherein said recording of said pressure/temperature curve is carried out by the said means to determine the variation of pressure as a function of time.

12. Process according to claim 11, characterised by the fact that on the recording there is determined at least one of the following values:

the height of a recorded peak, the surface area of a recorded peak, the length of the test up to the end of development of said bubble or the appearance of a leak therein.

* * * * *